(12) United States Patent
Lee

(10) Patent No.: US 7,700,275 B2
(45) Date of Patent: Apr. 20, 2010

(54) DETECTION SYSTEM

(75) Inventor: Martin Alan Lee, Salisbury (GB)

(73) Assignee: The Secretary of State of Defense, Salisbury, Witshire (GB)

( * ) Notice: Subject to any disclaimer, the term of this patent is extended or adjusted under 35 U.S.C. 154(b) by 654 days.

(21) Appl. No.: 10/478,788

(22) PCT Filed: May 24, 2002

(86) PCT No.: PCT/GB02/02443

§ 371 (c)(1),
(2), (4) Date: Jun. 8, 2004

(87) PCT Pub. No.: WO02/097132

PCT Pub. Date: Dec. 5, 2002

(65) Prior Publication Data

US 2004/0241679 A1 Dec. 2, 2004

(30) Foreign Application Priority Data

May 25, 2001 (GB) ................................. 0112868.5

(51) Int. Cl.
*C12Q 1/68* (2006.01)
(52) U.S. Cl. .......................... 435/6; 435/91.1; 435/91.2
(58) Field of Classification Search ....................... None
See application file for complete search history.

(56) References Cited

U.S. PATENT DOCUMENTS

| | | | |
|---|---|---|---|
| 3,183,157 A | 5/1965 | Bhuyan et al. |
| 3,997,662 A | 12/1976 | Pinnert et al. |
| 4,012,284 A | 3/1977 | DiMarco et al. |
| 4,197,249 A | 4/1980 | Murdock et al. |
| 4,469,863 A | 9/1984 | Ts'o et al. |
| 4,868,103 A | 9/1989 | Stavrianopoulos et al. |
| 5,132,327 A | 7/1992 | Patterson |
| 5,200,313 A | 4/1993 | Carrico |
| 5,208,323 A | 5/1993 | Page et al. |
| 5,491,063 A | 2/1996 | Fisher et al. |
| 5,567,583 A | 10/1996 | Wang et al. |
| 5,658,548 A | 8/1997 | Padhye et al. |
| 5,858,397 A | 1/1999 | Lim et al. |
| 6,106,777 A | 8/2000 | Fujita et al. |
| 6,403,311 B1 | 6/2002 | Chan |
| 6,833,257 B2 | 12/2004 | Lee et al. |
| 7,090,977 B2 | 8/2006 | Yun et al. |
| 7,354,706 B2 | 4/2008 | Rowlen et al. |
| 7,364,858 B2 | 4/2008 | Barany et al. |
| 2002/0106682 A1 | 8/2002 | Lee et al. |
| 2002/0119455 A1 | 8/2002 | Chan |
| 2004/0241679 A1 | 12/2004 | Lee |
| 2005/0112647 A1 | 5/2005 | Lee et al. |
| 2006/0127906 A1 | 6/2006 | Lee |
| 2006/0286570 A1 | 12/2006 | Rowlen et al. |
| 2007/0009954 A1 | 1/2007 | Wang et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |

FOREIGN PATENT DOCUMENTS

| | | |
|---|---|---|
| EP | 0 063 879 | 11/1982 |
| EP | 0512334 | 11/1992 |
| EP | 0512334 A2 * | 11/1992 |
| EP | 0 566 751 | 10/1993 |
| EP | 0 699 768 A1 | 3/1996 |
| EP | 0 745 690 A2 | 12/1996 |
| EP | 0 872 562 A1 | 10/1998 |
| GB | 9725197.9 | 11/1997 |
| GB | 2333359 * | 7/1999 |
| GB | 2333596 | 7/1999 |
| GB | 2334904 | 9/1999 |
| GB | 2338301 | 12/1999 |
| GB | 2 365 866 A | 2/2002 |
| GB | 0223563.8 | 10/2002 |
| JP | 2000-509608 | 8/2000 |
| WO | WO 88/02004 | 3/1988 |
| WO | WO 95 08642 A2 | 3/1995 |

(Continued)

OTHER PUBLICATIONS

Thelwell et al. Nucleic Acids Research vol. 28:3752-3761. 2000.*
N. Thelwell, et al., "Mode of action and application of Scorpion primers to mutation detection," Nucleic Acids Research, vol. 28, No. 19, pp. 3752-3761, 2000.
Agrawal, et al., 'Efficient methods for attaching non-radioactive labels to the 5' ends of synthetic oligodeoxyribonucleotides,' *Nucleic Acids Research*, 14:6227 (1986).

(Continued)

*Primary Examiner*—Heather G Calamita
(74) *Attorney, Agent, or Firm*—Kilpatrick Stockton LLP

(57) ABSTRACT

A method for detecting the presence of a target nucleic acid sequence in a sample, said method comprising: performing nucleic acid amplification on the sample in the presence of (a) a DNA duplex binding agent, (b) a nucleic acid polymerase and (c) a reagent comprising an amplification primer which can hybridize to said target sequence when in single stranded form and which is connected at its 5' end to a probe which carries a label by way of a chemical linking group, said labeled probe being of a sequence which is similar to that of the said target nucleic acid sequence, such that it can hybridize to a complementary region in an amplification product, and wherein the label is able to absorb fluorescence from or donate fluorescent energy to the DNA duplex binding agent; and monitoring fluorescence of said sample.

17 Claims, 11 Drawing Sheets

FOREIGN PATENT DOCUMENTS

Figure 1A:
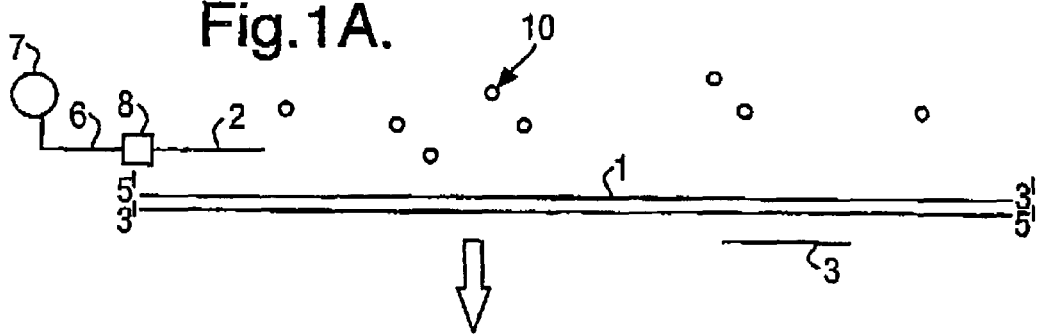
Figure 1B:
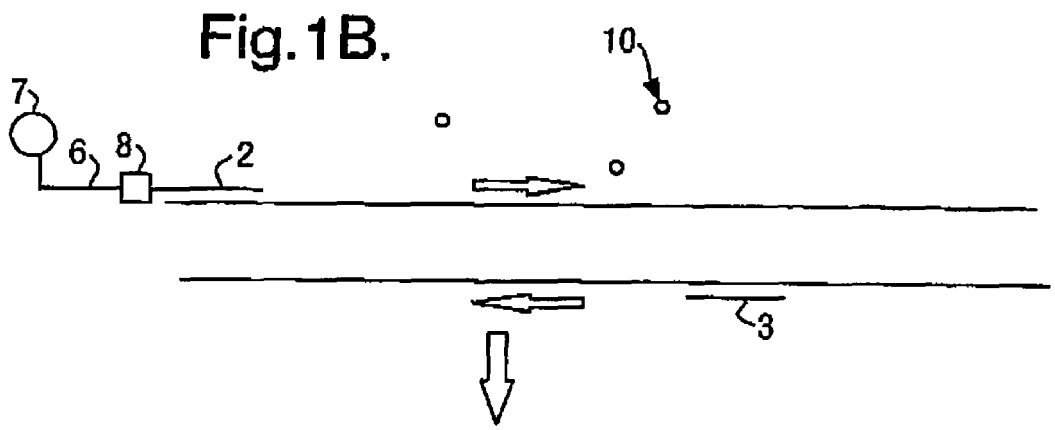

| WO | WO 97/12030 A | | 4/1997 |
|---|---|---|---|
| WO | WO 97/46714 | | 12/1997 |
| WO | WO 98/02449 | | 1/1998 |
| WO | WO 99/28500 | | 6/1999 |
| WO | WO 99/28500 A1 | | 6/1999 |
| WO | WO 99 42611 | * | 8/1999 |
| WO | WO 99/42611 | | 8/1999 |
| WO | WO 99/66071 | * | 12/1999 |
| WO | WO 01/11078 | | 2/2001 |
| WO | WO 01 86001 | | 11/2001 |
| WO | WO 02/088387 | | 7/2002 |
| WO | WO 02/097132 | | 12/2002 |
| WO | WO 2004/033726 | | 4/2004 |

OTHER PUBLICATIONS

Alberts, et al., Molecular Biology of the Cell, Second Edition (1989), pp. 165-166.

Bassam, et al., 'Nucleic Acid Sequence Detection Systems: Revolutionary Automation for Monitoring and Reporting PCR Products,' *Australasian Biotechnology*, 6:5:285(1996).

Becker, et al., 'A Quantitative Method of Determining Initial Amounts of DNA by Polymerase Chain Reaction Cycle Titration Using Digital Imaging and a Novel DNA Stain,' *Analytical Biochemistry*, 237:204-207 (1996).

Bergstrom, et al., 'C-5 Substituted Pyrimidine Nucleosides, 2. Synthesis via Olefin Coupling to Organopalladium Intermediates Derived from Uridine and 2'-Deoxyuridine,' *J. Amer. Chem. Soc.*, 10:8106 (1978).

Betz, Promega document, 'Single-cell RT-PCR using RNasin® Ribonuclease Inhibitor,' pp. 1-4 (Mar. 15, 2006).

Bigge, et al., 'Palladium-Catalyzed Coupling Reactions of Uracil Nucleosides and Nucleotides,' *J. Amer. Chem. Soc.*, 102:2033 (1980).

Cardullo, et al., 'Detection of nucleic acid hybridization by nonradiative fluorescence resonance energy transfer ,' *Proc. Natl. Acad. Sci. USA*, 85:8790-8794 (1988).

Chou, et al., 'Use of dark-quenched FRET probes in real-time PCR,' *American Biotechnology Laboratory*, vol. 19, p. 34 (2001).

Gelmini, et al., 'Quantitative polymerase chain reaction-based homogeneous assay with fluorogenic probes to measure c-erbB-2 oncogene amplification,' *Clinical Chemistry*, 43(5):752-758 (1997).

Idziorek, et al., 'YOPRO-1 permits cytofluorometric analysis of programmed cell death (apoptosis) without interfering with cell viability,' *Journal of Immunological Methods*, 185:249-258 (1995).

Klebe, et al., 'RT-PCR without RNA isolation,' *Biotechniques*, 21(6):1094-100 (1996), Abstract Only.

Marrazza, et al. 'Disposable DNA electrochemical sensor for hybridization detection,' *Biosensors and Bioelectronics*, 14:43-51 (1999).

Morrison, et al., 'Solution-Phase Detection of Polynucleotides Using Interacting Fluorescent Lables and Competitive Hybridization,' *Analytical Biochemistry*, 183:231-244 (1989).

Morrison, et al., 'Chemluminescent and Fluorescentg Probes for DNA Hybridization Systems,' *Rapid Detection and Identification of Infectious Agents*, 245-256 (1985).

Morrison, et al., Nonisotopic DNA Probe Techniques, Chapter 13:311-315 (1992), Edited by Larry J. Kricka, Academic Press, Inc.

Ranasinghe, et al., 'Linear fluorescent oligonucleotide probes with an acridine quencher generate a signal upon hybridization,' *Chem. Commun.*, 1480-1481 (2001).

Ruth, et al., 'C-5 Substituted Pyrimidine Nucleosides. 1. Synthesis of C-5 Allyl, Propyl, and Propenyl Uracil and Cytosine Nucleosides via Organopalladium Intermediates,' *J. Org. Chem.*, 43:2870 (1978).

Slateva, et al., 'HLA-DRB fluorotyping by dark quenching and automated analysis,' *Tissue Antigens*, 58:250-254 (2001).

Smith, et al., 'Mitoxantrone-DNA binding and the induction of Topolsomerase II associated DNA Damage in Multi-drug resistant small cell lung cancer cells,' *Biochem. Pharma.*, 40(9):2069-2078 (1990).

Strahan & Read, Human Molecular Genetics 2, pp. 104-105 (1999).

Vaughan, et al., 'Human Antibodies with Sub-nanomolar Affinities Isolated from a Large Non-immunized Phage Display Library,' *Nature Biotechnology*, 14:309 (1996).

Wallace, et al., 'Hybridization of synthetic oligodeoxyribonucleotides to Ix174: the effect of single base pair mismatch,' *Nucleic Acids Research*, 6(11):3543-3557 (1979).

Werntges, et al., 'Mismatches in DNA double strands: thermodynamic parameters and their correlations to repair efficiencies,' *Nucleic Acids Research*, 14(9):3773-3790 (1986).

Wilson, et al., 'Snapback SSCPAnalysis: Engineered Conformation Changes for the Rapid Typing of Known Mutations,' Human Mutation, Wiley-Liss, New York, NY, 11:252-258 (1998).

Wittwer, et al., 'BioFeatures: Continuous Fluorescence Monitoring of Rapid Cycle DNA Amplification,' *BioTechniques*, 22(1):130-138 (1997).

Yamane, 'MagiProbe: a novel fluorescence quenching-based oligonucleotide probe carrying a fluorophore and a intercalator,' *Nucleic Acids Research*, 30(19):1-8 (2002).

Zhang, et al., 'Reconstruction of DNA sequencing by hybridization,' *Bioinformatics*, 19(1):14-21 (2003).

Catalogue entry from Invitrogen, Molecular Probes—Catalog of Cell Biology Products—Plasma MembraneIntegrity, pp. 1-7 (Jun. 12, 2005).

Front page from a Promega Technical bulletin, 'DNA Purification System,' (2005).

Applied Biosystems: Catalog, Applied Biosystems Product Information Page, Power SYBR® Green PCR Master Mix, pp. 1-2 (Nov. 22, 2005).

Applied Biosystems: Catalog, Applied Biosystems Ordering Information Page, Power SYBR® Green PCR Master Mix, p. 1 (Nov. 22, 2005).

Molecular Probes, Section 8.4 'Nucleic Acid Detection and Quantitation in Electrophoretic Gels and Capillaries,' pp. 1-11 (Nov. 22, 2005).

Observation for Supplying Prior Publications.

Office Action dated Sep. 29, 2005 in related U.S. Appl. No. 10/958,377.

Response dated Mar. 29, 2006 in related U.S. Appl. No. 10/958,377.

Office Action dated Jun. 26, 2006 in related U.S. Appl. No. 10/958,377.

Response dated Jul. 12, 2006 in related U.S. Appl. No. 10/958,377.

Office Action dated Sep. 8, 2006 in related U.S. Appl. No. 10/958,377.

Response dated Mar. 8, 2007 in related U.S. Appl. No. 10/958,377.

Office Action dated Mar. 26, 2007 in related U.S. Appl. No. 10/958,377.

Response dated Sep. 26, 2007 in related U.S. Appl. No. 10/958,377.

Petition Dec dated Oct. 5, 2007 in related U.S. Appl. No. 10/958,377.

Response dated Oct. 25, 2007 in related U.S. Appl. No. 10/958,377.

Advisory Action dated Oct. 25, 2007 in related U.S. Appl. No. 10/958,377.

Response dated Nov. 23, 2007 in related U.S. Appl. No. 10/958,377.

Office Action dated Jun. 12, 2008 in related U.S. Appl. No. 10/958,377.

Interview Summary dated Jul. 10, 2008 in related U.S. Appl. No. 10/958,377.

Communication dated Sep. 24, 2008 in related U.S. Appl. No. 10/958,377.

Didenko, et al., "DNA Probes Using Fluorescence Resonance Energy Transfer (FRET): Designs and Applications", Biotechniques 2001, vol. 31(5), 1106-1121.

Lee, et al., "ResonSense®:Simple Fluorescent Probes for Quantitative Homogeneous Rapid Polymerase Chain Reaction", Analytica Chimica Acta 2002, vol. 457, 61-70.

* cited by examiner

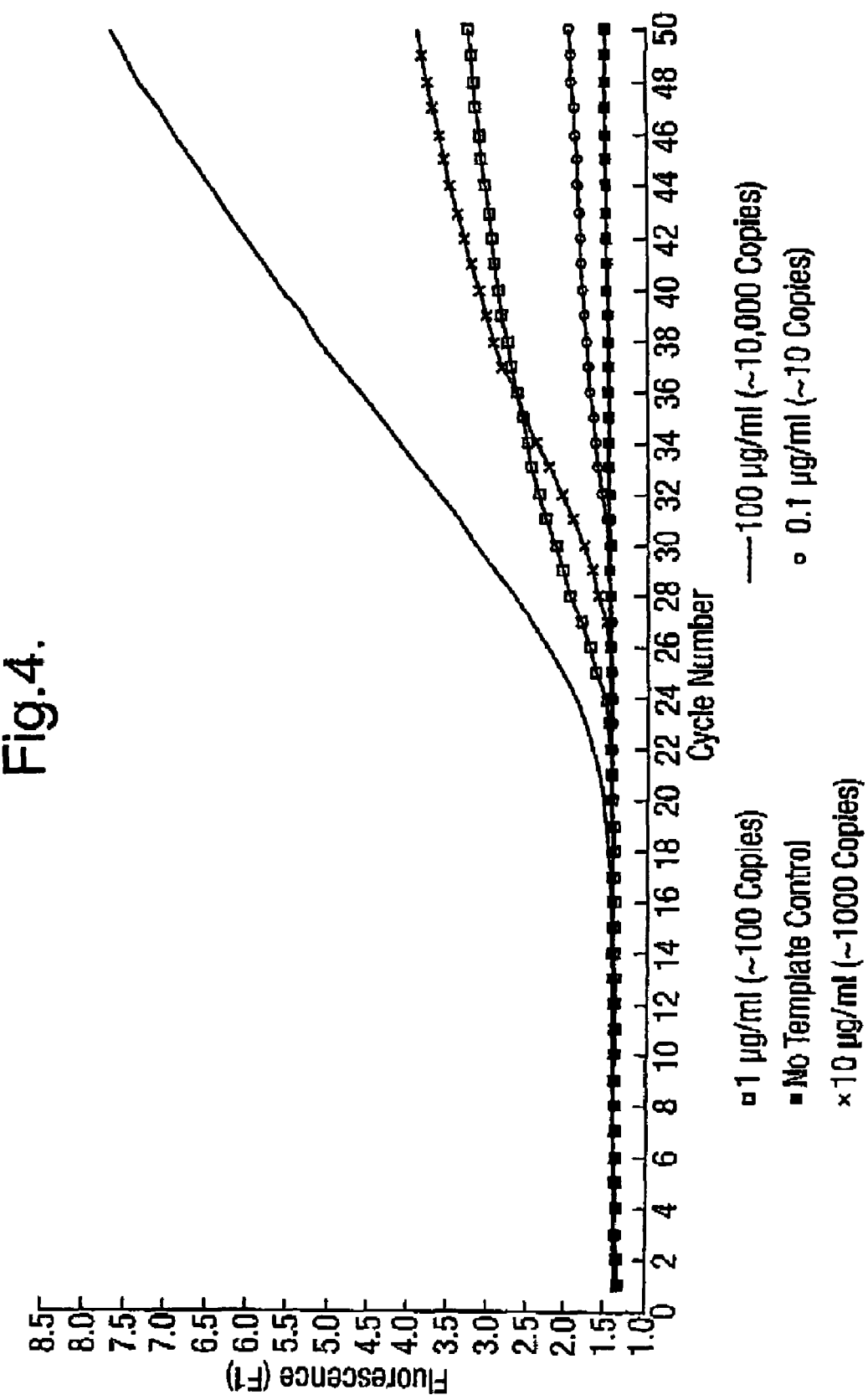

DETECTION SYSTEM

CROSS REFERENCE TO RELATED APPLICATIONS

This application is the U.S. national phase of International Application No. PCT/GB02/02443 filed on May 24, 2002 and published in English as International Publication No. WO 02/097132 A2 on Dec. 5, 2002, which application claims priority to Great Britain Application No. 0112868.5 filed on May 25 2001, the contents of which are incorporated by reference herein.

The present invention provides a method for detecting a target polynucleotide in a sample, for example by monitoring an amplification reaction, preferably in a quantitative manner, as well as to kits for use in these methods. The method is also suitable for the detection of sequence characteristics such as polymorphisms or allelic variation and so may be used in diagnostic methods.

Known fluorescence polymerase chain reaction (PCR) monitoring techniques include both strand specific and generic DNA intercalator techniques that can be used on a few second-generation PCR thermal cycling devices.

Generic fluorescence PCR methods utilise DNA intercalating dyes that exhibit increased fluorescence when bound to double stranded DNA species. An increase in fluorescence due to a rise in the bulk concentration of DNA during amplifications can be used to measure reaction progress and to determine the initial target molecule copy number. Furthermore, by monitoring fluorescence with a controlled change of temperature, DNA melting curves can be generated, for example, at the end of PCR thermal cycling.

These generic fluorescence PCR methods monitor the rise in bulk concentration of nucleic acids without any time penalty. A single fluorescent reading can be taken at the same point in every reaction. End point melting curve analysis can be used to discriminate artefacts from amplicon, and to discriminate amplicons. Peaks of products can be seen at concentrations that cannot be visualised by agarose gel electrophoresis.

It has been found that DNA melting curve analysis in general is a powerful tool in optimising PCR thermal cycling. By determining the melting temperatures of the amplicons, it is possible to lower the denaturing temperatures in later PCR cycles to this temperature. Optimisation for amplification from first generation reaction products rather than the genomic DNA, reduces artefact formation occurring in later cycles. Melting temperatures of primer oligonucleotides and their complements can be used to determine their annealing temperatures, reducing the need for empirical optimisation.

The generic intercalator methods however are only quasi-strand-specific and are therefore not very useful where strand specific detection is required.

Fluorescence PCR strand specific methods utilise additional nucleic acid reaction components to monitor the progress of amplification reactions. These methods may use fluorescence energy transfer (FET) as the basis of detection. One or more nucleic acid probes are labelled with fluorescent molecules, one of which is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is excited at this emission wavelength such that it can accept the emission energy of the donor molecule by a variety of distance-dependent energy transfer mechanisms. A specific example of fluorescence energy transfer which can occur is Fluorescence Resonance Energy Transfer or "FRET". Generally the acceptor molecule accepts the emission energy of the donor molecule when they are in close proximity (e.g. on the same, or a neighbouring molecule). The basis of FET or FRET detection is to monitor the changes at donor emission wavelength. Where the acceptor is also a fluorescent molecule, the acceptor emission wavelengths may also be monitored.

There are two commonly used types of FET or FRET probes, those using hydrolysis of nucleic acid probes to separate donor from acceptor, and those using hybridisation to alter the spatial relationship of donor and acceptor molecules.

Hydrolysis probes are commercially available as TaqMan™ probes. These consist of DNA oligonucleotides which are labelled with donor and acceptor molecules. The probes are designed to bind to a specific region on one strand of a PCR product. Following annealing of the PCR primer to this strand, Taq enzyme extends the DNA with 5' to 3' polymerase activity. Taq enzyme also exhibits 5' to 3' exonuclease activity. TaqMan™ probes are protected at the 3' end by phosphorylation to prevent them from priming Taq extension. If the TaqMan™ probe is hybridised to the product strand than an extending Taq molecule may also hydrolyse the probe, liberating the donor from acceptor as the basis of detection. The signal in this instance is cumulative, the concentration of free donor and acceptor molecules increasing with each cycle of the amplification reaction.

The fact that signal generation is dependent upon the occurrence of probe hydrolysis reactions means that there is a time penalty associated with this method. Furthermore, the presence of the probe may interrupt the smooth operation of the PCR process.

In addition, it has been found that hydrolysis can become non-specific, particularly where large numbers of amplification cycles, for instance more than 50 cycles, are required. In these cases, non-specific hydrolysis of the probe will result in an unduly elevated signal.

This means that such techniques are not very compatible with rapid PCR methods which are becoming more prominent with the development of rapid hot air thermal cyclers such as the RapidCycler™ and LightCycler™ from Idaho Technologies Inc. Other rapid PCR devices are described for example in co-pending British Patent No. 2334904. The merits of rapid cycling over conventional thermal cycling have been reported elsewhere. Such techniques are particularly useful for example in detection systems for biological warfare where speed of result is important if loss of life or serious injury is to be avoided.

Furthermore, hydrolysis probes do not provide significant information with regard to hysteresis of melting since signal generation is, by and large, dependent upon hydrolysis of the probe rather than the melt temperature of the amplicon or probe.

Hybridisation probes are available in a number of guises. Molecular beacons are oligonucleotides that have complementary 5' and 3' sequences such that they form hairpin loops. Terminal fluorescent labels are in close Proximity for FRET to occur when the hairpin structure is formed. Following hybridisation of molecular beacons to a complementary sequence the fluorescent labels are separated, so FRET does not occur, and this forms the basis of detection.

Pairs of labelled oligonucleotides may also be used. These hybridize in close proximity on a PCR product strand bringing donor and acceptor molecules together so that FRET can occur. Enhanced FRET is the basis of detection. Variants of this type include using a labelled amplification primer with a single adjacent probe.

The use of two probes, or a molecular beacon type of probe which includes two labelling molecules increases the cost involved in the process. In addition, this method requires the presence of a reasonably long known sequence so that two probes which are long enough to bind specifically in close proximity to each other are known. This can be a problem in some diagnostic applications, where the length of conserved sequences in an organism which can be used to design an effective probe may be relatively short such as the HIV virus.

Furthermore, the use of pairs of probes involves more complex experimental design. For example, a signal provided by the melt of a probe is a function of the melting off of both probes. The study of small mismatches or where one of the probes is required to bind across a splice region (for example to detect RNA as compared to DNA in a sample where the sequence on either side of an intron can be utilised as the probe site) can yield incorrect results if the other probe melts first.

Co-pending international application WO99/28500 describes a method for detecting the presence of a particular target nucleic acid sequence, the method comprising a) adding to the sample a probe specific for said sequence, the probe bearing a moiety able to either donate fluorescence to, or absorb fluorescent energy from, a DNA duplex binding agent, b) subjecting the mixture to a amplification reaction, c) hybridising the probe to the target sequence and monitoring the fluorescence from the sample. The reaction can then be monitored by measuring the fluorescence of said sample as this will alter during the course of the reaction as more product is formed which hybridises to the probe and gives rise to a FET or FRET interaction between the DNA duplex binding agent and the fluorescent moiety on the probe.

Co-pending International Patent application No. PCT/GB99/00504 describes a similar assay for detecting the presence of particular nucleic acid sequences which may be adapted to quantify the amount of the target sequence in the sample. In this assay, an amplification reaction is effected using a set of nucleotides, at least one of which is fluorescently labelled. Thus the amplification product has fluorescent label incorporated in it. The reaction is effected in the presence of a probe which can hybridise to the amplification product and which includes a reactive molecule which is able to absorb fluorescence from or donate fluorescent energy to said fluorescent labelled nucleotide. The reaction can then be monitored by measuring the fluorescence of said sample as this will alter during the course of the reaction as more product is formed which hybridises to the probe and gives rise to a FET or FRET interaction between them.

International Patent Application WO01/11078 describes a further related method for detecting the presence of a target nucleic acid sequence in a sample. In this assay, in a first stage, the target sequence is made single stranded so that the primer region of the reagent can hybridise to it. This can thus initiate extension of the strand to generate a complementary strand which will include labelled nucleotides and will also have a labelled probe region upstream of its 5' end which is complementary to a downstream region of the product. Once the extension phase is complete, the product is separated from its template strand during a melt phase and so becomes single stranded. In this form, the labelled probe region is able to twist over and hybridise to the complementary region of the product strand whereupon the label which is able to donate fluorescent energy (donor) to the other label by means of FET or FRET does so, thus changing the fluorescent signal from the sample. This change in signal can be monitored throughout the reaction in order to monitor the progress of the amplification reaction.

Assays comprising the use of Scorpion probe systems are disclosed in GB2338301 and Nucleic Acids Research, 2000, vol. 28, no. 19, 3752-3761. The Scorpion probe systems comprise a primer portion attached to a probe portion by a linking moiety. The probe systems comprise both donor and acceptor moieties. In this assay, in a first stage, the target sequence is made single stranded so that the primer portion can hybridise to the target sequence. This can thus initiate extension of the strand to generate a complementary strand which will have the probe portion upstream of its 5' end which is complementary to a downstream region of the product. Once the extension phase is complete, the product is separated from its template strand during a melt phase and so becomes single stranded. In this form, the labelled probe region is able to twist over and hybridise to the complementary region of the product strand. The hybridisation of the probe portion to the complementary region of the product strand alters the spatial relationship between the donor and acceptor moieties and thus the fluorescent signal from the sample is changed.

The applicants have now found an alternative improved assay.

The present invention provides a method for detecting the presence of a target nucleic acid sequence in a sample, said method comprising:

performing nucleic acid amplification on the sample in the presence of (a) a DNA duplex binding agent, (b) a nucleic acid polymerase and (a) a reagent comprising an amplification primer which can hybridise to said target sequence when in single stranded form and which is connected at its 5' end to a probe which carries a label by way of a chemical linking group, said labelled probe being of a sequence which is similar to that of the said target nucleic acid sequence, such that it can hybridise to a complementary region in an amplification product, and wherein the label is able to absorb fluorescence from or donate fluorescent energy to the DNA duplex binding agent; and monitoring fluorescence of said sample.

The present invention is cheaper and simpler than the prior art assay of WO01/11078 and is surprisingly effective. In the present invention, the DNA duplex binding agent is added to the reaction mixture in an unbound state, dispensing with the Reed to attach the agent either to a nucleotide, as in WO01/11078, or to the probe system as in GB2338301.

In the assay of the present invention, in a first stage, the target sequence is made single stranded so that the primer region of the reagent can hybridise to it. This can thus initiate extension of the strand to generate a complementary strand. The primer strand will also have a labelled probe region upstream of its 5' end which is complementary to a downstream region of the product. DNA duplex binding material (preferably an intercalating dye) will become entrapped within the duplex so formed. Once the extension phase is complete, the product is separated from its template strand during a melt phase and so becomes single stranded. In this form, the labelled probe region is able to twist over and hybridise to the complementary region of the product strand, thus entrapping DNA duplex binding agent between probe region and complementary region of the product strand. Due to the mutual proximity of the DNA duplex binding agent and the probe label, the fluorescent moiety which is able to donate fluorescent energy (donor) to the acceptor moiety by means of FET or FRET does so, thus changing the fluorescent signal from the sample. This change in signal can be monitored throughout the reaction in order to monitor the progress of the amplification reaction.

In the second and subsequent stages of the amplification, the product strand may itself act as a template strand for extension. However, the chemical link between probe and primer will halt the extension reaction before a sequence complementary to said probe is produced. Thus the probe region remains single stranded.

It is preferred that the method of the present invention comprises:

(a) adding to a sample suspected of containing the target nucleic acid sequence, the DNA duplex binding agent, the nucleic acid polymerase and the reagent;

(b) subjecting said sample to conditions under which the primer hybridises to the target nucleic acid sequence and an amplification product comprising the probe is formed;

(c) subjecting said sample to conditions under which the labelled probe hybridises to a complementary region in the amplification product; and (d) monitoring fluorescence of said sample during at least one of steps (b) and (c).

If required, a corresponding amplification primer which is not attached to a labelled probe region may also be present during the amplification reaction. This primer would result in the production of a conventional unlabelled amplification product which may serve to mediate the signal into the dynamic range of the detector device being used. It may also improve reaction efficiency which may be adversely affected by the presence of a complex probe/primer structure.

When the acceptor label which is able to absorb fluorescence from the donor label performs this function, fluorescence from the donor is reduced. This reduction may be detected and this indicates binding of the probe region.

Most preferably, the label which is able to absorb fluorescence acceptor) is itself a fluorescent molecule which emits fluorescence at a characteristic wavelength. Such probes include a rhodamine dye or Cy5. In this case, increase in fluorescence from the acceptor molecule, which is of a different wavelength to that of the donor label, will also indicate binding of the probe. Alternatively, the acceptor does not fluoresce (dark acceptor). Such acceptors include DABCYL, methyl red, QSY-7 diarylrhodamine dyes and 6-(dimethylamino)-2-[4-[4-(dimethylamino)phenyl]-1,3-butadienyl]-1-ethyl quinolinium perchlorate (CAS number 181885-68-7).

Suitably, the DNA duplex binding agent comprises a donor label and the acceptor label is provided on the probe. In this case, and if the acceptor fluoresces, then the presence of the thus labelled amplification product can be detected by monitoring fluorescence from the acceptor molecule on the probe, which predominantly binds to a downstream region of the same product strand. In this case, signal from the amplification product can be distinguished from background signal of the fluorescent label and also from any non-specific amplification product. Alternatively, the DNA duplex binding agent may comprise an acceptor label and the probe comprises the donor label.

In the system of the present invention there is discrimination between the rise in the generic intercalator signal (as the DNA is amplified) and the sequence specific signal which is only generated when the two fluorescent moieties are in close proximity (i.e. when probe hybridises to amplification product). The fact that the sequence specific signal is produced only by labelled amplification product means that the system is highly specific in terms of detecting specific target sequences in reaction mixtures that contain large amounts of background DNA. This is because non-specific amplification product will not hybridise to the probe region and so does not contribute to the measured signal. The measurement of the generic intercalator signal in addition to the sequence specific signal may be beneficial. The generic intercalator signal is proportional to the degree of amplification in the reaction mixture and thus may be used to indicate the efficiency or blockage of amplification.

An assay of this nature can be carried out using inexpensive reagents. Single labelled probes are more economical than those which include both acceptor and donor molecules.

Amplification is suitably effected using known amplification reactions such as the polymerase chain reaction (PCR) or the ligase chain reaction (LCR), strand displacement assay (SDA) or NASBA, but preferably PCR.

Preferably, the fluorescence of both the donor and the acceptor moieties are monitored and the relationship between the emissions calculated.

The position of the label along the probe is immaterial although it general, they will be positioned at an end region of the probe. More than one label may be used in the reagent, but one is preferred since it is cheaper.

In order for FET, such as FRET, to the fluorescent emission of the donor moiety must be of a shorter wavelength than the acceptor moiety.

Suitable combinations are therefore set out in the following Table:

| Donor | Acceptor |
| --- | --- |
| SYBRGold | Rhodamine |
| SYBRGreen I | Rhodamine |
| Fluorescein | Rhodamine |
| SYBRGold | Cy5 |
| SYBRGreen I | Cy5 |
| Fluorescein | Cy5 |
| Fluorescein | Ethidium bromide |
| Fluorescein | Dabcyl |
| Fluorescein | Methyl Red |
| Fluorescein | QSY-7 diaryl rhodamine dyes* |
| SYBRGold | Cy5.5 |

*Available from Molecular Probes, UK.

Those skilled in the art will realise that many other such combinations are possible.

Preferably, the molecules used as donor and/or acceptor produce sharp emission peaks, and there is little or no overlap in the wavelengths of the emission, Under these circumstances, it may not be necessary to resolve the "strand specific peak" from the signal produced by amplification product. A simple measurement of the strand specific signal alone (i.e. that provided by the acceptor moiety) will provide information regarding the extent of the FET or FRET caused by the target reaction.

However, where there is a spectral overlap in the fluorescent signals from the donor and acceptor moieties, this can be accounted for in the results, for example by determining empirically the relationship between the spectra and using this relationship to normalise the signals from the two signals.

The chemical link separating the labelled probe from the primer is suitably any molecule that can link nucleotide sequences but which is not recognised by a DNA polymerase. A wide range of chemical linkers which would fulfil this requirement are available.

Examples of the types of chemical and reactions which may be used in the formation of linkers are described for example in WO 95/08642. In particular, the chemical linker comprises a group of atoms joining the two polynucleotide sequences, primer and probe, together. The linker can be joined to the respective polynucleotide sequences by any of the conventional methods.

Generally speaking, the linker will be derived from an organic chemical having a first and a second functional group by means of which it can be attached to the probe and the primer sequences respectively or to individual nucleotides from which the probe or primer sequence is then generated subsequently. The linker is generally designed not to bind to nucleotides.

The synthesis of linkers is discussed in detail in, for example, S. Agrawal et al, Nucleic Acids Research, 1986, 14, 6227 and WO-88/02004 (Applied Biosystems); J. L. Ruth and p. E. Bergstrom, J. Org. Chem., 1978, 43, 2870; D. E. Bergstrom and M. K. Ogawa, J. Amer. Chem. Soc., 1978, 10, 8106; and C. F. Bigge, P. Kalaritis, J. R. Deck and M. P. Mertes, J. Amer. Chem. Soc., 1980, 102, 2033; and European Patent Application No. 063,879. The reader is also directed to International Patent Application WO01/11078 for a more detailed discussion of the structure and synthesis of reagents having chemical linking groups that join a probe and primer.

In particular, the linkers will comprise a multiple form of ethylene glycol, for example hexaethylene glycol (HEG). Such linkers may be of structure —(CHOH—CHOH)$_n$— where n is an integer in excess of 1, for example from 1-10 and suitably 6.

Such reagents comprising linker groups that link a probe and primer can be obtained from Oswel Research Products Ltd, UK.

The method of the present invention is extremely versatile in its applications. The method can be used to generate both quantitative and qualitative data regarding the target nucleic acid sequence in the sample, as discussed in more detail hereinafter. In particular, not only does the invention provide for quantitative amplification, but also it can be used, additionally or alternatively, to obtain characterising data such as duplex destabilisation temperatures or melting points.

In the method of the invention, the labelled probe is integral with an amplification primer and so is present throughout the course of the amplification reaction. The process allows the detection to be effected in a homogenous manner, in that the amplification and monitoring can be carried out in a single container with all reagents added initially. No subsequent reagent addition steps are required. It may be possible to use the method of the present invention in some heterogeneous systems. Note that there is no need to effect the method in the presence of solid supports (although this is an option as discussed further hereinafter).

Since the probe is present throughout the amplification reaction, the fluorescent signal may allow the progress of the amplification reaction to be monitored. This may provide a means for quantitating the amount of target sequence present in the sample.

If a fluorescent acceptor moiety is used, then during each cycle of the amplification reaction, amplicon strands containing the target sequence and a probe region generate an acceptor signal. As the amount of such amplicons in the sample increases, so the acceptor signal will increase. By plotting the rate of increase over cycles, the start point of the increase can be determined.

The labelled probe may comprise a nucleic acid molecule such as DNA or RNA, which will hybridise to the target nucleic acid sequence when the latter is in single stranded form. In this instance, conditions will be used which render the target nucleic acid single stranded. Alternatively, the probe may comprise a molecule such as a peptide nucleic acid or another nucleic acid analogue which also binds the target sequence in double stranded form.

In particular, the amplification reaction used will involve a step of subjecting the sample to conditions under which any of the target nucleic acid sequence present in the sample becomes single stranded, such as PCR or LCR. It is possible then for the probe region to hybridise to the downstream region of the amplicon strand containing it during the course of the amplification reaction provided appropriate hybridisation conditions are encountered.

In a preferred embodiment, the probe may be designed such that these conditions are met during each cycle of the amplification reaction. Thus at some point during each cycle of the amplification reaction, the probe will hybridise to the target sequence, and generate a signal as a result of the FET or FRET. As the amplification proceeds, the probe region will be separated or melted from the downstream sequence and so the signal generated by the acceptor label will either reduce or increase depending upon whether it comprises the donor or acceptor molecule. For instance, where it is an acceptor, in each cycle of the amplification, a fluorescence peak from the acceptor label is generated. The intensity of the peak will increase as the amplification proceeds because more amplicon strands including probes becomes available.

By monitoring the fluorescence of the acceptor label from the sample during each cycle, the progress of the amplification reaction can be monitored in various ways. For example, the data provided by melting peaks can be analysed, for example by calculating the area under the melting peaks and this data plotted against the number of cycles.

Fluorescence is suitably monitored using a known fluorimeter. The signals from these, for instance in the form of photomultiplier voltages, are sent to a data processor board and converted into a spectrum associated with each sample tube. Multiple tubes, for example 96 tubes, can be assessed at the same time. Data may be collected in this way at frequent intervals, for example once every 10 ms, throughout the reaction.

The spectra generated in this way can be resolved, for example, using "fits" of pre-selected fluorescent moieties such as dyes, to form peaks representative of each signalling moiety (i.e. DNA duplex binding agent and/or probe label). The areas under the peaks can be determined which represents the intensity value for each signal, and if required, expressed as quotients of each other. The differential of signal intensities and/or ratios will allow changes in FET or FRET to be recorded through the reaction or at different reaction conditions, such as temperatures. The changes, as outlined above, are related to the binding phenomenon between the probe and the target sequence. The integral of the area under the differential peaks will allow intensity values for the FET or FRET effects to be calculated.

These data provide one means to quantitate the amount of target nucleic acid present in the sample.

The Primer/labelled probe reagent may either be free in solution or immobilised on a solid support, for example on the surface of a bead such as a magnetic bead, useful in separating products, or the surface of a detector device, such as the waveguide of a surface plasmon resonance detector and, for example, a DNA array. The selection will depend upon the nature of the particular assay being examined and the particular detection means being employed.

The probe may be designed such that it is hydrolysed by the DNA polymerase used in the amplification reaction thereby releasing the acceptor molecule. This provides a cumulative signal, with the amount of free probe label present in the system increasing with each cycle. However, it is not necessary in this assay for the probe to be consumed in this way as the signal does not depend upon the hydrolysis of the probe.

Suitably, the probe is designed such that it is released intact from the target sequence and so is able to bind again when suitable hybridisation conditions are met during the amplification reaction. This may be, for example, during the extension phase of the amplification reaction. However, since the signal is tot dependent upon probe hydrolysis, the probe may be designed to hybridise and melt from the target sequence at any stage during the amplification cycle. In particular, the probe may preferably be designed to hybridise at temperatures below the extension temperature of the reaction as this will ensure that interference with the amplification reaction is minimised.

This provides a fully reversible signal which is directly related to the amount of amplification product present at each stage of the reaction. Furthermore, it is advantageous where speed of reaction is of the greatest importance, for example in rapid PCR, since a probe which is integral with the amplicon strand being detected will be able to hybridise rapidly to it.

The data generated in this way can be interpreted in various ways. In its simplest form, an increase in fluorescence of the acceptor molecule in the course of or at the end of the amplification reaction is indicative of an increase in the amount of the target sequence present, suggestive of the fact that the amplification reaction has proceeded and therefore the target sequence was in fact present in the sample. However, as outlined above, quantification is also possible by monitoring the amplification reaction throughout. Finally, it is possible to obtain characterisation data and in particular melting point analysis, either as an end point measure or throughout, in order to obtain information about the sequence as will be discussed further below.

Thus, a preferred embodiment of the invention comprises a method for detecting nucleic acid amplification comprising: performing nucleic acid amplification on a target polynucleotide in the presence of (a) a nucleic acid polymerase, (b) a DNA duplex binding agent and (c) a reagent comprising an amplification primer which can hybridize to said target sequence when in single stranded form and which is connected at its 5' end to a probe which carries a second label, by way of a chemical linking group, said labelled probe being of a sequence which is similar to that of the said target sequence, such that it can hybridise to a complementary region in an amplification product, and wherein one of the DNA duplex binding agent or second label comprises a donor label which is able to donate fluorescent energy to the other of the DNA duplex binding agent or second label which comprises an acceptor label able to absorb fluorescent energy from said donor molecule, said primer being capable of hybridising to said target polynucleotide; and monitoring changes in fluorescence during the amplification reaction.

Suitably, the acceptor label is itself fluorescent and emits fluorescent energy at a characteristic wavelength. The amplification is suitably carried out using a pair of primers which are designed such that only the target nucleotide sequence within a DNA strand is amplified as is well understood in the art. The nucleic acid polymerase is suitably a thermostable polymerase such as Taq polymerase.

Suitable conditions under which the amplification reaction can be carried out are well known in the art. The optimum conditions may be variable in each case depending upon the particular amplicon involved, the nature of the primers used and the enzymes employed. The optimum conditions may be determined in each case by the skilled person. Typical denaturation temperatures are of the order of 95° C., typical annealing temperatures are of the order of 55° C. and extension temperatures are of the order of 72° C.

In a particular embodiment of the invention the labelled probe may be used to quantitate RNA transcripts, for example in expression experiments, that may be used in drug discovery. In particular this embodiment is suitable for expression studies in tissues from eukaryotic organisms. DNA encoding proteins in eukaryotic cells may contain introns, non-coding regions of DNA sequence, and axons that encode for protein sequence. Non-coding intron sequences are removed from RNA sequences that are derived from the DNA sequences during cellular "splicing" processes. PCR primers are normally targeted at coding regions and when reverse transcriptase PCR is used on total nucleic acid extracts, products will result from both DNA dependent amplification and RNA dependent amplification. Thus PCR alone, when used for expression studies, will contain amplification resulting from genomic DNA and expressed RNA.

A labelled probe that is designed to bind across introns, on adjacent terminal regions of coding exons, will have limited interaction because of the intron region. Spliced RNA has these regions removed and therefore the adjacent terminal regions of coding axons form one continuous sequence allowing efficient binding of the probe region.

Conversely, the probe region may detect only an amplification product of genomic DNA if it is designed such that it binds an intron region. Signal generated from such a probe would relate only to the DNA concentration and not the RNA concentration of the sample. It is also possible to use two reagents, each having different probes and primers, one reagent suitable for use with the splice region of the RNA and one reagent suitable for the intron in the DNA.

Thus in a further embodiment, the probe region is specific either for a splice region of RNA or an intron in DNA, so that only one of amplified RNA or amplified DNA is detected and/or quantitated.

Alternatively or additionally, the method of the invention can be used in hybridisation assays for determining characteristics of a sequence. Thus in a further aspect, the invention provides a method for determining a characteristic of a nucleic acid sequence, said method comprising (a) amplifying said sequence in the presence of a DNA duplex binding agent and a reagent comprising an amplification primer linked by way of a chemical link at its end to a probe which comprises a sequence which is similar to that of a region of the target sequence and which further comprises a label, where one of said DNA duplex binding agent and the label is a donor label and the other is an acceptor label, the donor label being able to donate fluorescent energy to the acceptor label; so as to form an amplification product incorporating a probe region, (b) subjecting amplification product to conditions under which the probe region thereof will hybridise to the complementary region of the amplification product, and (c) monitoring fluorescence of said sample and determining a particular reaction condition, characteristic of said sequence, at which fluorescence changes as a result of the hybridisation of the probe region to the sample or destabilisation of the duplex formed between the probe region and the target nucleic acid sequence.

Suitable reaction conditions include temperature, electrochemical, or the response to the presence of particular enzymes or chemicals. By monitoring changes in fluorescence as these properties are varied, information characteristic of the precise nature of the sequence can be achieved. For example, in the case of temperature, the temperature at which the probe separates from the sequences in the sample as a result of heating can be determined. This can be extremely useful in for example, to detect and if desired also to quantitate, polymorphisms and/or allelic variation in genetic diagnosis. By "polymorphism" is included transitions, transversions, insertions, deletions of inversions which may occur in sequences, particularly in nature.

The hysteresis of melting will be different if the target sequence varies by only one base pair. Thus for example, where a sample contains only a single allelic variant, the temperature of melting of the probe region will be a particular value which will be different from that found in a sample which contains only another allelic variant. A sample containing both allelic variants which show two melting points corresponding to each of the allelic variants.

Thus, in a further embodiment of the present invention a method for detecting a polymorphism and/or allelic variation, said method comprising amplifying a sequence suspected of containing said polymorphism or variation using a method of the present invention, measuring the temperature at which the probe region melts from its complementary sequence within the amplification product using the fluorescent signal generated, and relating this to the presence of a polymorphism or allelic variation.

Similar considerations apply with respect to electrochemical properties, or in the presence of certain enzymes or chemicals. The labelled probe may be immobilised on a solid surface across which an electrochemical potential may be applied. Downstream target sequence will bind to or be repulsed from the probe at particular electrochemical values depending upon the precise nature of the sequence.

In addition, the kinetics of probe hybridisation will allow the determination, in absolute terms, of the target sequence concentration. Changes in fluorescence from the sample can allow the rate of hybridisation of the probe region to the sample to be calculated. An increase in the rate of hybridisation will relate to the amount of target sequence present in the sample. As the concentration of the target sequence increases as the amplification reaction proceeds, hybridization of the probe region will occur more rapidly. Thus this parameter may also be used as a basis for quantification. This mode of data processing useful in that it is not reliant directly on signal intensity to provide the information.

In a further embodiment of the invention, a kit for use in the method of the present invention which kit comprises a reagent comprising an amplification primer linked at its 5' end by way of a chemical link, to a probe specific for a target nucleotide sequence, wherein the probe comprises a first label which may act as one of either a donor and acceptor label; and a DNA intercalating agent comprising a second label, which second label may act as one of either a donor and acceptor label, wherein the first and second labels form a donor-acceptor pair.

If desired, the probe can be immobilised on a support such as a bead, for example a magnetic bead, or a support used in a detector, such as the waveguide of an evanescent wave detector device. Other potential components of the kit include reagents used in amplification reactions such as a DNA polymerase.

The use of a non-fluorescent acceptor molecule may also be used in the assay described in co-pending International Patent Application No PCT/GB99/0504.

The present invention will now be particularly described by way of example with reference to the accompanying diagrammatic drawings in which:

FIG. 1 shows diagrammatically the molecular interactions which take place in the method of the invention.

Figure 5:
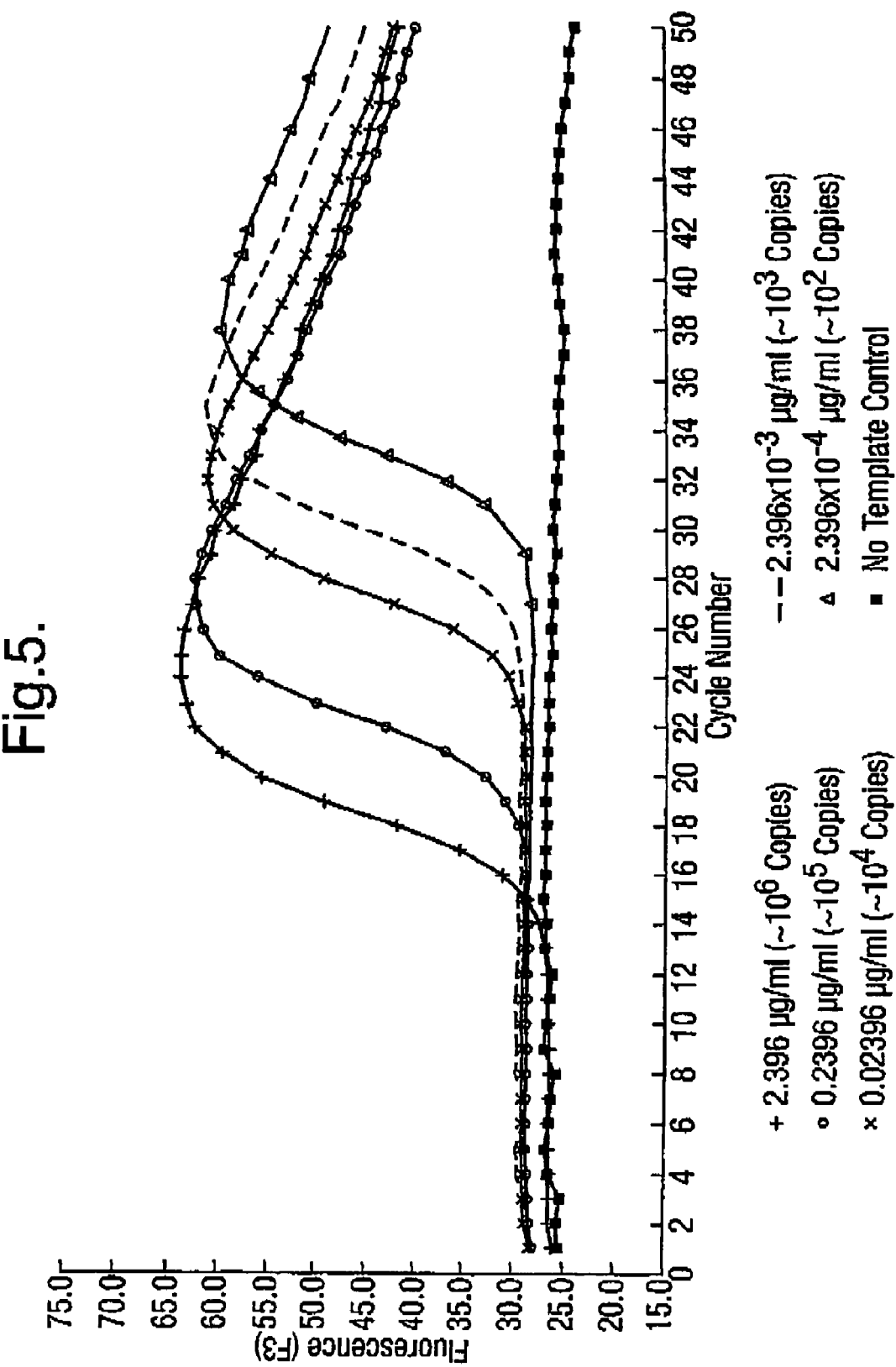
Figure 6:
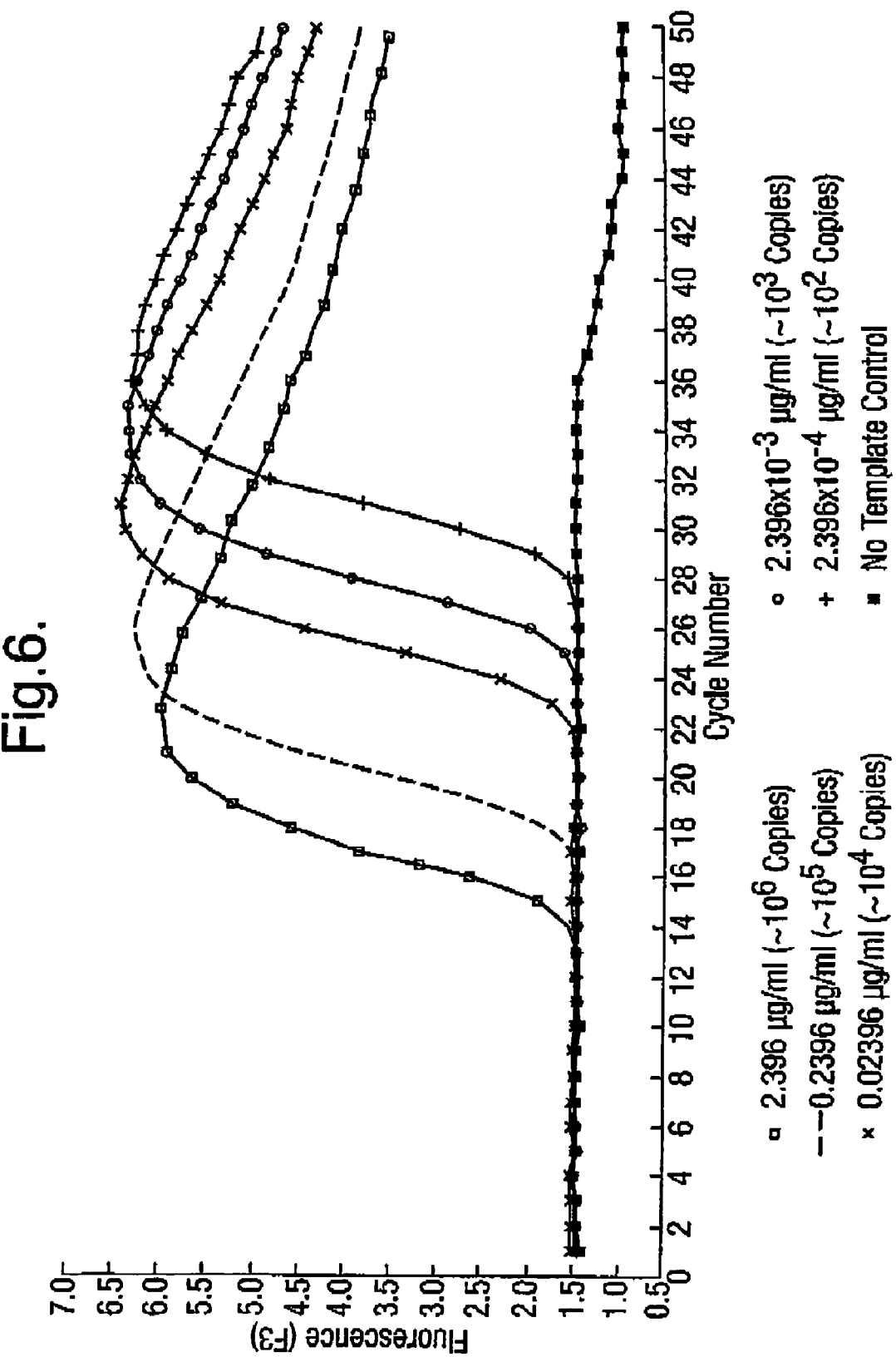
Figure 7:
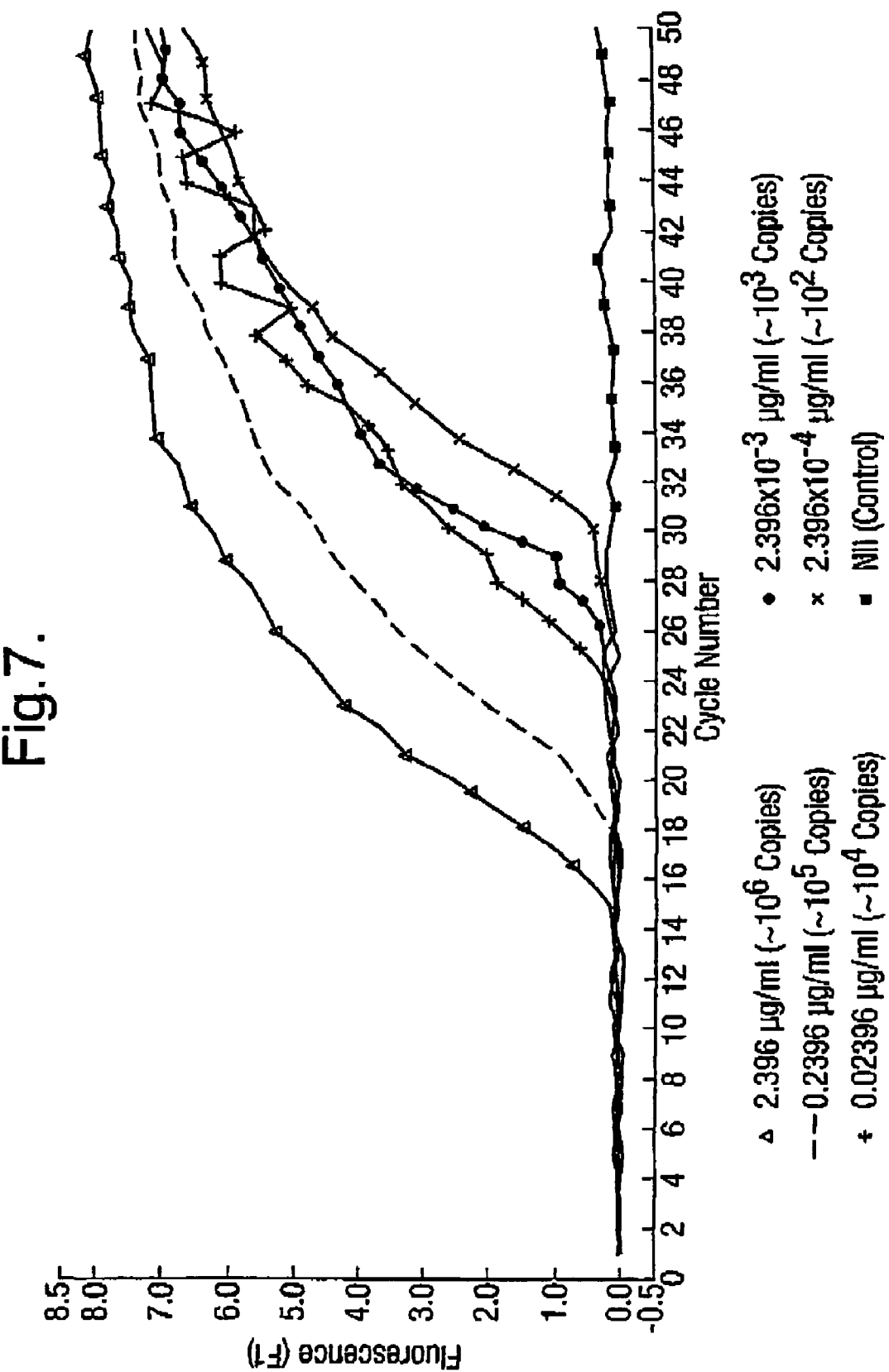
Figure 8:
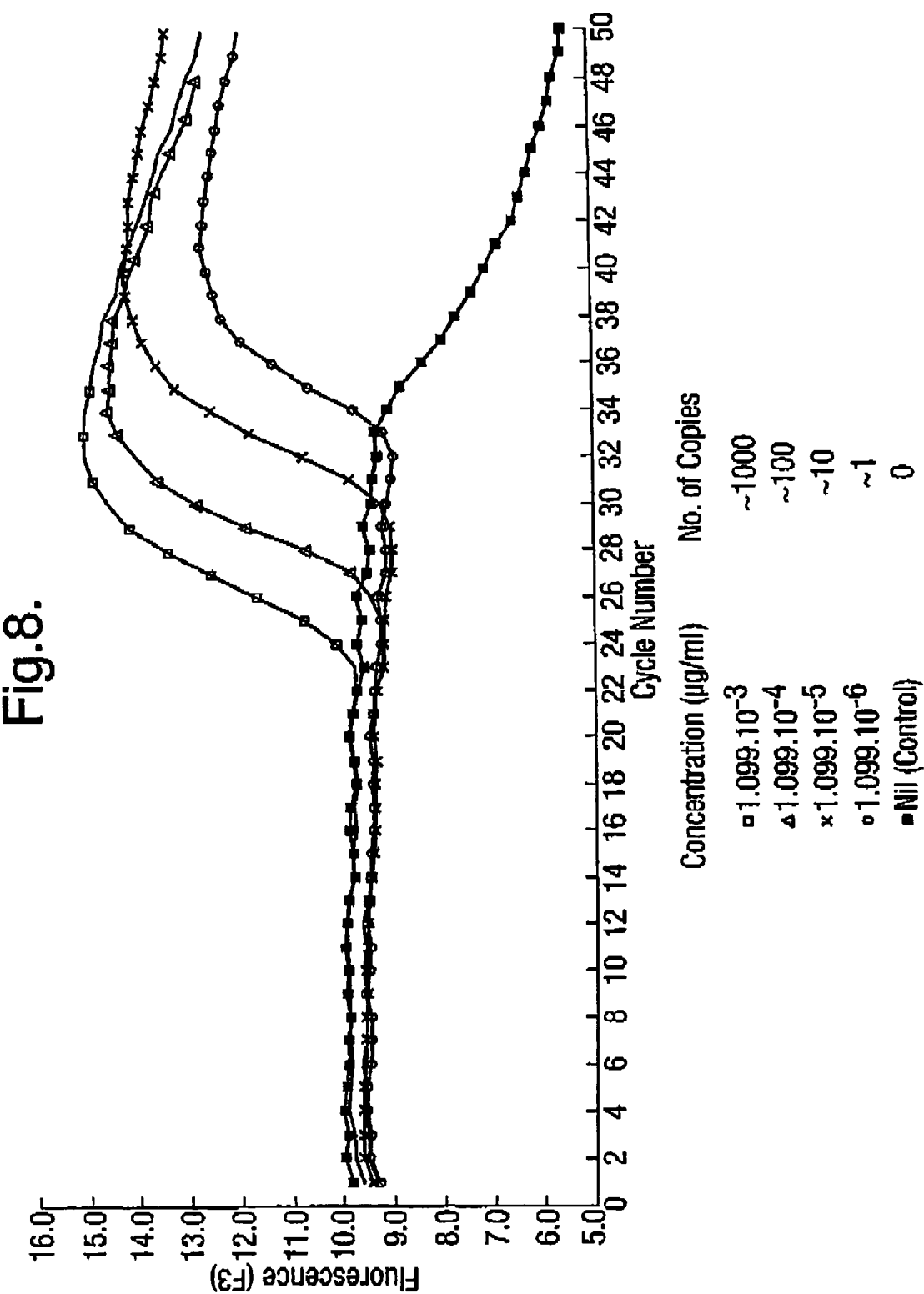
Figure 9:
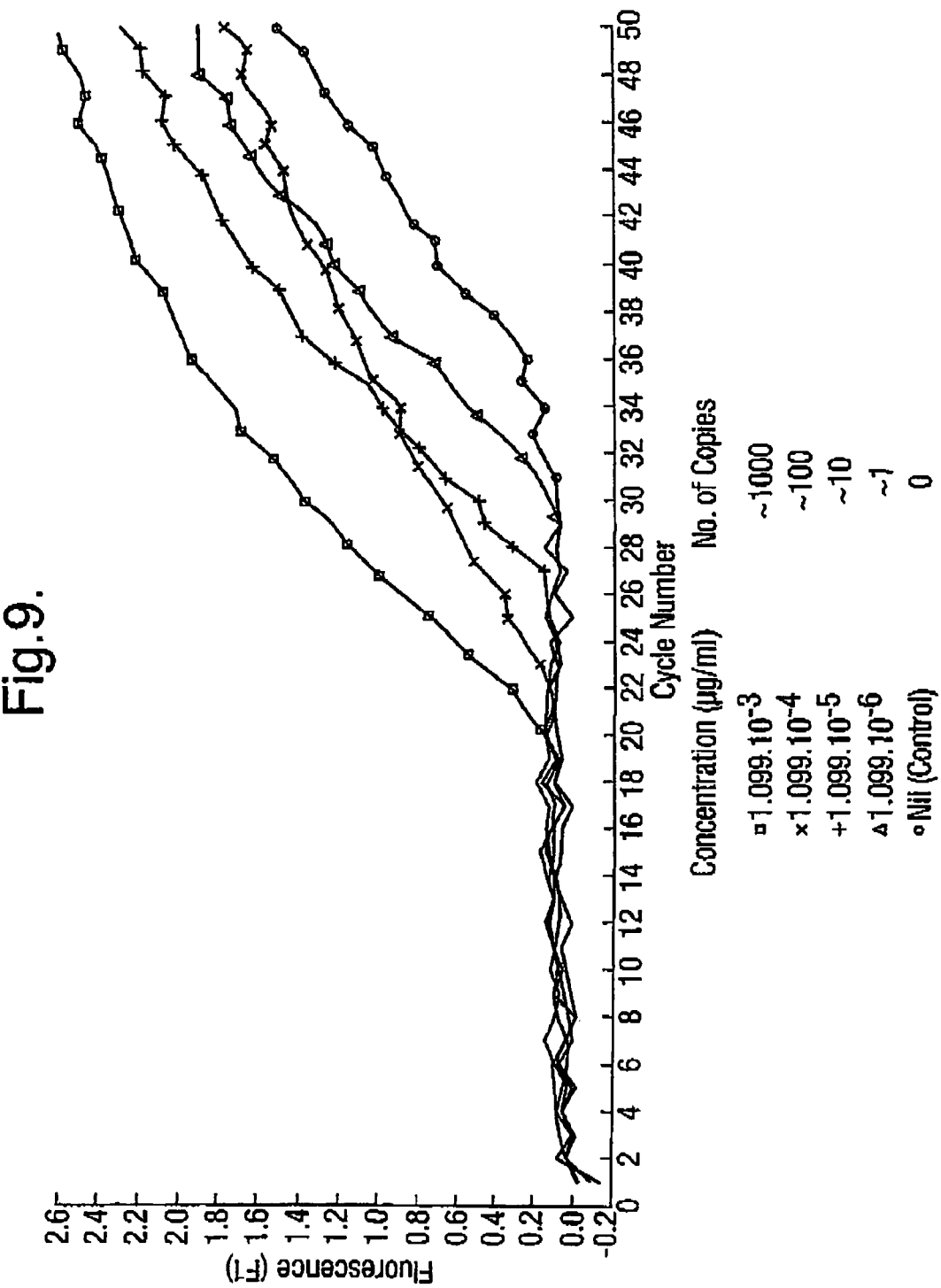
Figure 10:
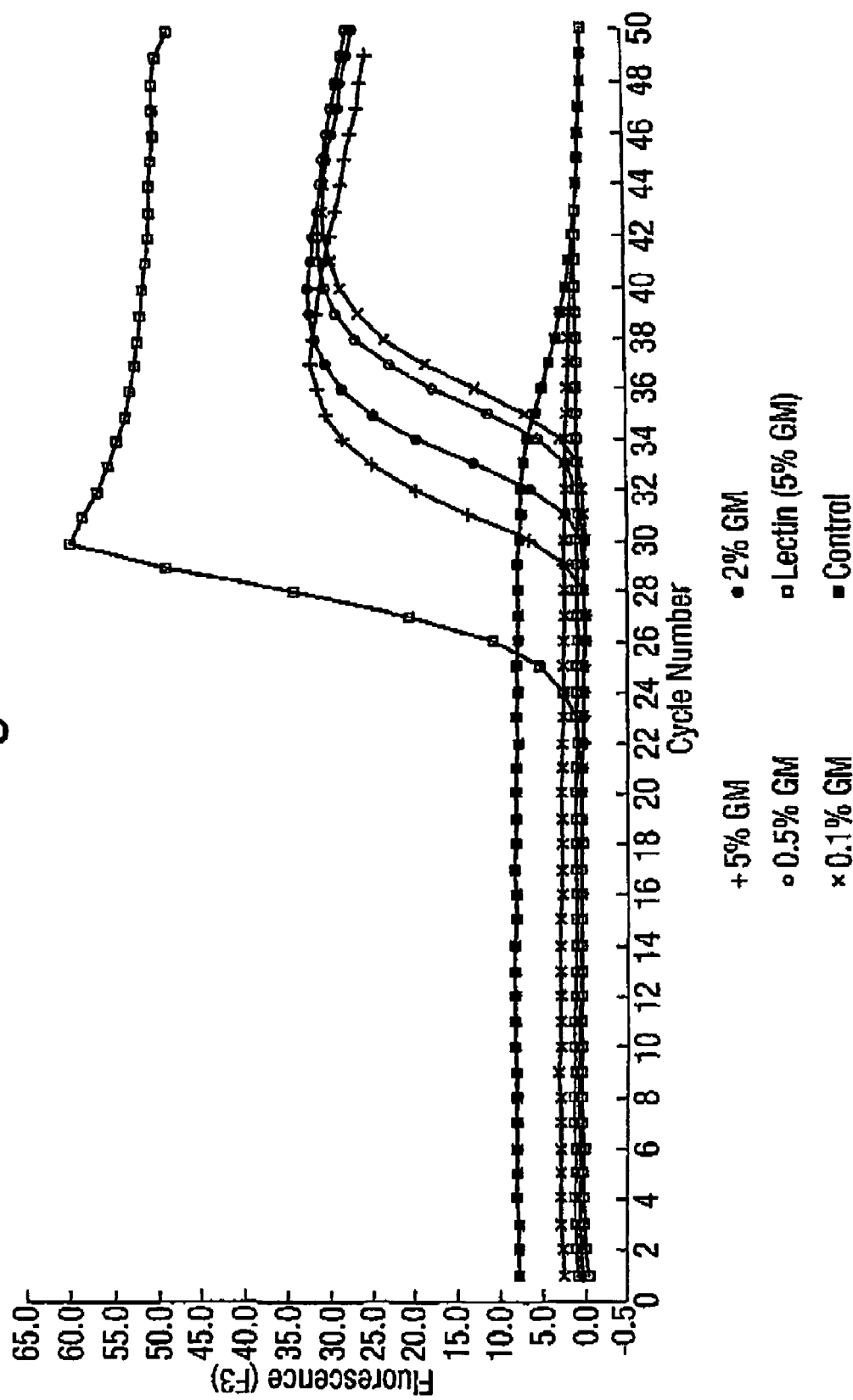
Figure 11:
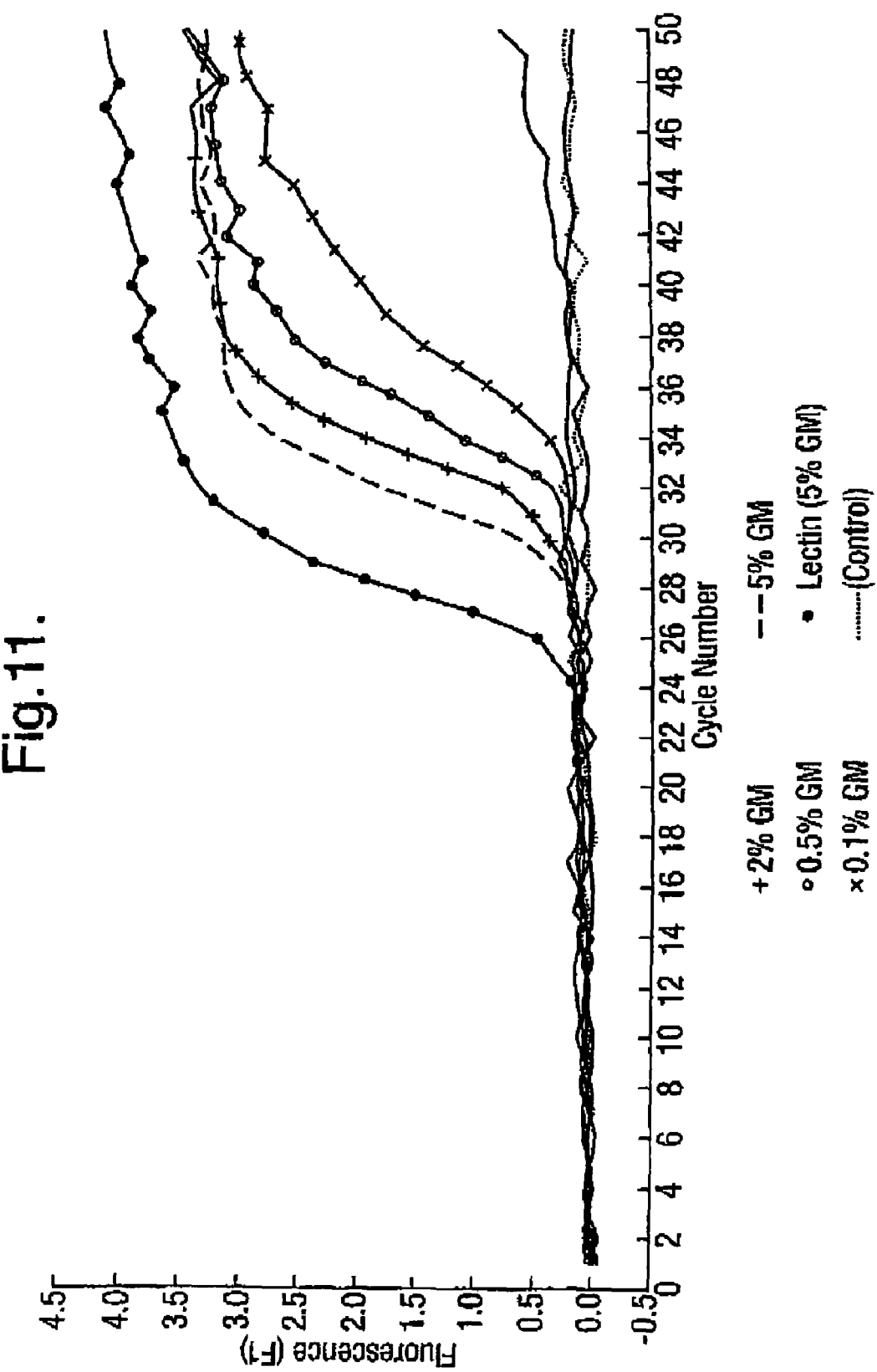

FIG. 2 shows fluorescence as measured in accordance with a method of the present invention by the F3 detector as a function of cycle number for the beta-actin system for various concentrations of human DNA FIG. 3 shows fluorescence as measured by the F3 detector in accordance with a comparative prior art method as a function of cycle number for the beta-actin system for various concentrations of human DNA FIG. 4 shows fluorescence as measured by the F1 detector using a Taqman™ method of the prior art as a function of cycle number for the beta-actin system for various concentrations of human DNA FIG. 5 shows fluorescence as measured in accordance with a method of the present invention by the F3 detector as a function of cycle number for a meningitis system for various concentrations of meningitis gene FIG. 6 shows fluorescence as measured by the F3 detector in accordance with a comparative prior art method as a function of cycle number for the meningitis system for various concentrations of meningitis gene FIG. 7 shows fluorescence as measured by the F1 detector using a Taqman™ method of the prior art as a function of cycle number for the meningitis system for various concentrations of meningitis gene FIG. 8 shows fluorescence as measured in accordance with a method of the present invention by the F3 detector as a function of cycle number for a chlamydia system for various concentrations of chlamydia gene FIG. 9 shows fluorescence as measured by the F1 detector using a Taqman™ method of the prior art as a function of cycle number for the chlamydia system for various concentrations of chlamydia gene FIG. 10 shows fluorescence as measured in accordance with a method of the present invention by the F3 detector as a function of cycle number for a genetically modified soybean system for various concentrations of modified gene; and FIG. 11 shows fluorescence as measured by the F1 detector using a Taqman™ method of the prior art as a function of cycle number for the GM soybean system for various concentrations of modified gene.

FIG. 1 shows diagrammatically the molecular interactions which take place in the method of the invention. In the illustrated amplification reaction, a DNA molecule (1) prepared for amplification by contacting it with pair of amplification primers (2), (3). One of the primers (2) is linked to a probe (6) which includes an acceptor label (7) by way of a chemical link (8) A fluorescent donor moiety (10) is provided in the reaction mixture.

The DNA molecule (1) is rendered single stranded (FIG. 1B) whereupon the primers (2,3) bind as forward and reverse primers respectively in an amplification reaction as is well known.

Figure 1C:
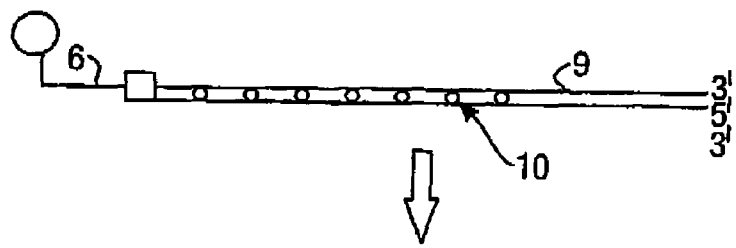

During the course of the subsequent amplification reaction, an amplicon product (9) is built up (FIG. 1C).

Figure 1D:
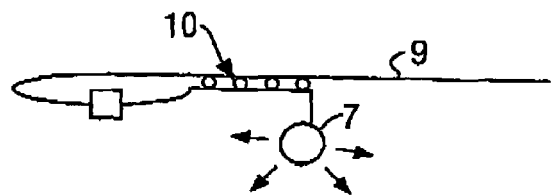

When this product is melted during the subsequent phase of the amplification, the probe region (6) comprising an acceptor label (7) binds the complementary region within the amplicon strand (FIG. 1D). Intercalator moieties (10) are entrapped between the probe and the product. The FRET interaction between the fluorescent intercalator moieties (10) and the acceptor label (7) generates a signal at the wavelength characteristic of the acceptor.

The signal from the acceptor molecule (7) can then be monitored using conventional fluorescence detection devices.

The person skilled in the art will realise that the use of the second primer (3) is not essential to the present invention.

Furthermore, those skilled in the art will realise that the label on the probe may be a donor label and the intercalator moiety may be an acceptor label.

PCR Amplification Reaction

PCR reaction mixtures contained the following reagents with working concentrations being prepared.

The composition was:

50 mM Trizma pH 8.8 at 25° C., 3 mM Magnesium Chloride, 8% w/Vol. Glycerol, 250 ng/µl non-acetylated bovine serum albumin, 200 µM dNTP's PCR nucleotides, 0.01 units/µl uracil-n-glycosylase, 0.04 units/µl Taq (exo 5'-3' deficient) DNA polymerase and 0.03 µM TaqStart anti-Taq antibody.

The Taq DNA polymerase and the TaqStart anti-Taq antibody were incubated together for minutes before addition to the mixture.

SYBRGold was included as the fluorescent donor label in the reactions to a final concentration of 1:20,000 to 1:200,000 dilution of the reference solution.

The Taq DNA polymerase was used to ensure that the reagent was not hydrolysed during the course of the reaction. The use of this polymerase was not found to be necessary because of the very short hold times used in the method of the present invention.

Target Template

Several target templates and associated genes were investigated. These are listed below.

| Target template | Gene |
| --- | --- |
| Human placental DNA | ABI human beta-actin amplicon |
| Soybean | Lel lectin |
| Genetically modified soybean | CP4 EPSPS |
| Neisseria meningitidis | porA |
| Chlamydia trachomatis | Ct plasmid |

Custom novel oligonucleotide reagents comprising probes and primers were made for each target gene. Each reagent has the generic structure: FL-PROBE-EEG-PRIMER, where FL is the fluorescent moiety, PROBE is the probe sequence, MEG is HEG (hexaethylene glycol) and PRIMER is the primer sequence which hybridises to the appropriate target sequence. The reagents are available from Oswel Research Products Ltd., UK. Reagents with the same generic structure suitable for use in the method of the present invention may be made in accordance with the teaching of WO01/11078.

The structure of the reagent corresponding to each gene is listed below:

| Gene | Reagent structure | |
| --- | --- | --- |
| Actin | $atgccctcccccatgccatcctgcgt*cagc ggaaccgctcattgccaatgg | (Seq No.1) |
| Lectin | $tgccttctttctcgcaccaattgaca*cctg catgtgtttgtggctt | (Seq. No.2) |
| CP4 | $ccttcatgttcggcggtctcgc*atgcgcgt ttcaccgct | (Seq. No.3) |
| PorA | $tcagcggcagcgtccaattcg*acttgctgt tttgggccg | (Seq. No.4) |
| PorA | $ccaaacgcacttccgccatcg*tcagccaag cgccagac | (Seq. No.5) |

-continued

| Gene | Reagent structure | |
| --- | --- | --- |
| Ct | $tatgcttacacatttatcgactgggtgatta cagc*ttttcgtctcttttcgcagc | (Seq. No.6) |

$—5' Cy5 label
*—HEG linking group

The concentration of the gene sequence to be detected was varied as desired. The final concentration of the reagent was 0.2 µM.

The performance of the method of the present invention was compared to methods of the prior art by repeating the experiments using analogous Taqman™ assays and those of WO99/28500.

The ThermalCycler real-time PCR instrument and consumables were obtained from Roche. The instrument was calibrated using conventional techniques. It was found to be extremely beneficial to run the colour calibration program with specific product and SYBRGold. It was also found to be beneficial to run the colour calibration program with Cy5.

The thermal cycling protocols were:

For the method of the present invention and that of WO99/28500:

50° C. hold for 1 minute for carry-over prevention

95° C. hold for 1 minute for initial denaturation 50 cycles of (95° C., 5 seconds; 60° C. 5 seconds; 74° C. 5 seconds, 5 seconds extension, collect fluorescence)

For the Taqman™ assays:

50° C. hold for 1 minute for carry-over prevention

95° C. hold for 1 minute for initial denaturation 50 cycles of (95° C., secs.; 60° C. 20-120 secs.; collect fluorescence at end of step)

This shows that the method of the present invention is considerably faster than that using the prior art TaqMan™ assays.

The ThermalCycler PCR instrument uses three detectors, denoted F1, F2 and F3. F1 operates at 520 nm, optimised to detect the emissions of SYBRGold and Fluorescein. F2 operates at 640 nm optimised to detect the signal generated by LC640. F3 operates at 705 nm, optimised to work with LC705.

The F1 (520 nm/Fluorescein) optical detector was used for detecting the non-strand specific amplification signal generated by the SYBRGold intercalating dye. The F3 (705 nm/LC705 dye) optical detector was used for detecting the amplification of specific product using the signal generated by the Cy5 moiety of the probe. The probe system used Cy5 instead of LC705 because of the better yield of incorporated dye during oligonucleotide synthesis.

EXAMPLE 1

Detection and Quantification of Beta-Actin Gene

FIG. 2 shows fluorescence as measured by the F3 detector as a function of cycle number for the beta-actin system for various concentrations of human DNA using the method of the present invention. Bach set of data shows a low-level background response for a given number of cycles, dependent on the concentration of DNA within the sample. Within each set of data, the observed fluorescence increases dramatically at a certain cycle number dependent on the concentration of human DNA in the sample. The fluorescence is generated by the probe section of the reagent binding to the amplification product downstream of the primer. This binding process brings the Cy5 moiety into proximity of the SYBRGold species. The SYBRGold species undergoes fluorescence, with the emitted light being adsorbed by the Cy5 moiety. The Cy5 itself then emits light which is detected by the F3 detector. As the cycle number further increases, the fluorescence reaches a maximum and then decreases slowly. It is believed that this is due to the probe section being displaced by amplification product (often referred to as the "hook effect" that is also observed in dual-hybe probe reporting chemistries).

Figure 2A:
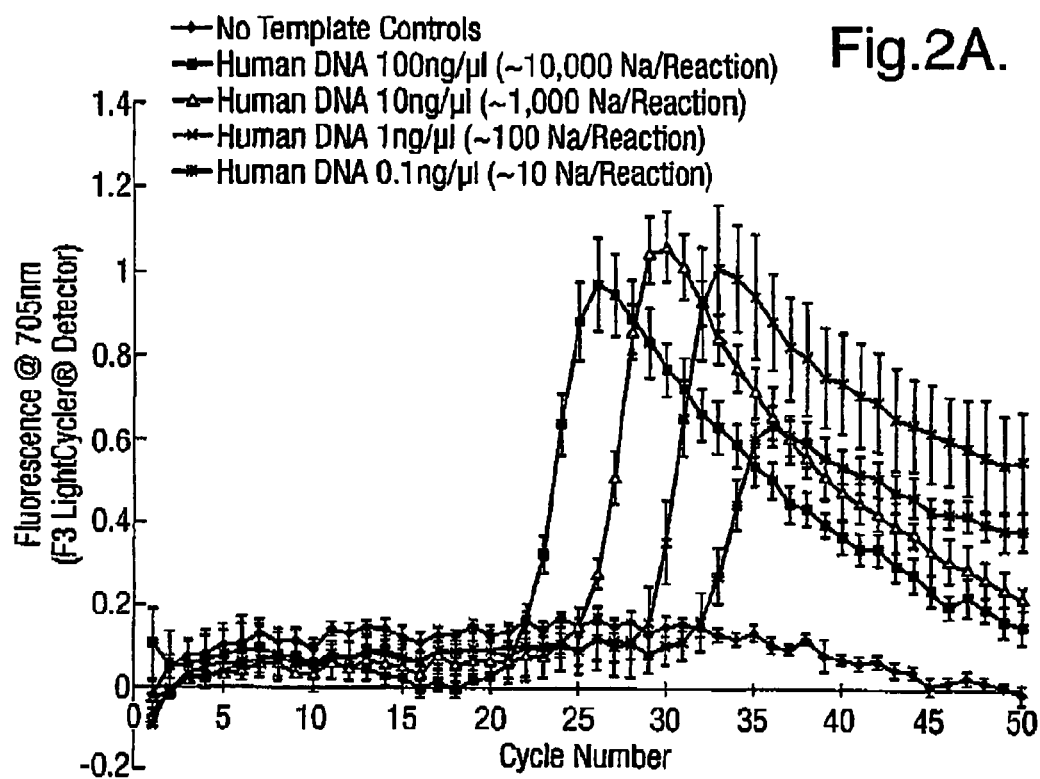
Figure 2B:
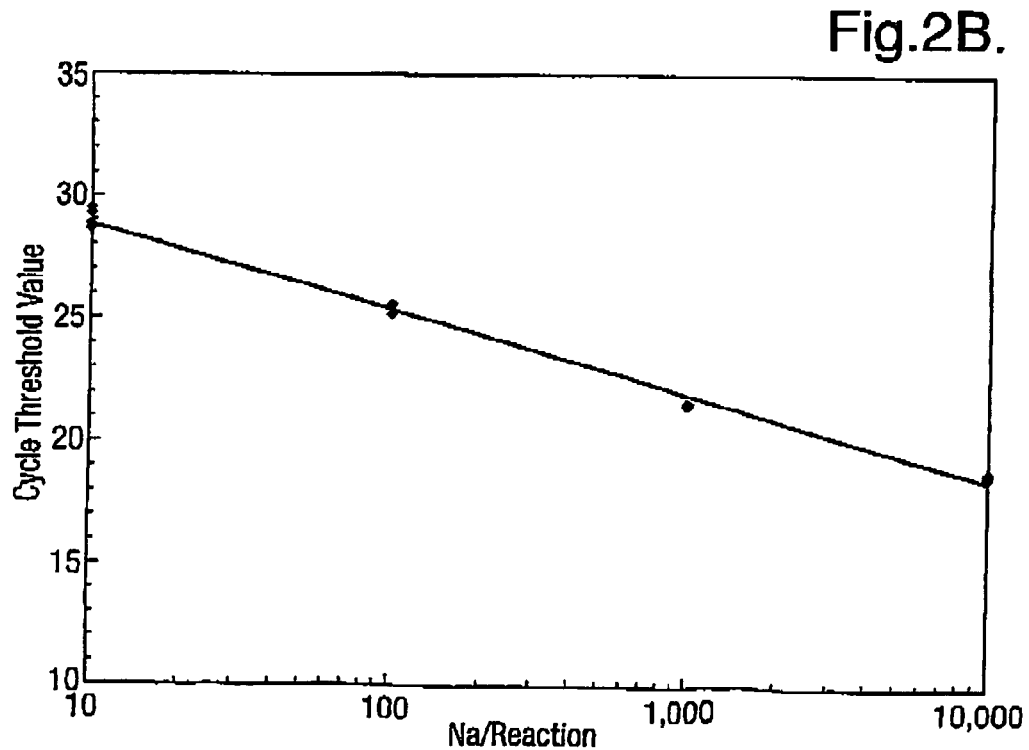

Analysis of the data sets of FIG. 2A produces a quantification curve as shown in FIG. 2B. The correlation co-efficient for the curve is near to 1.0, showing that the method of the present invention is excellent for quantification and identification of a nucleic acid sequence.

Figure 3A:
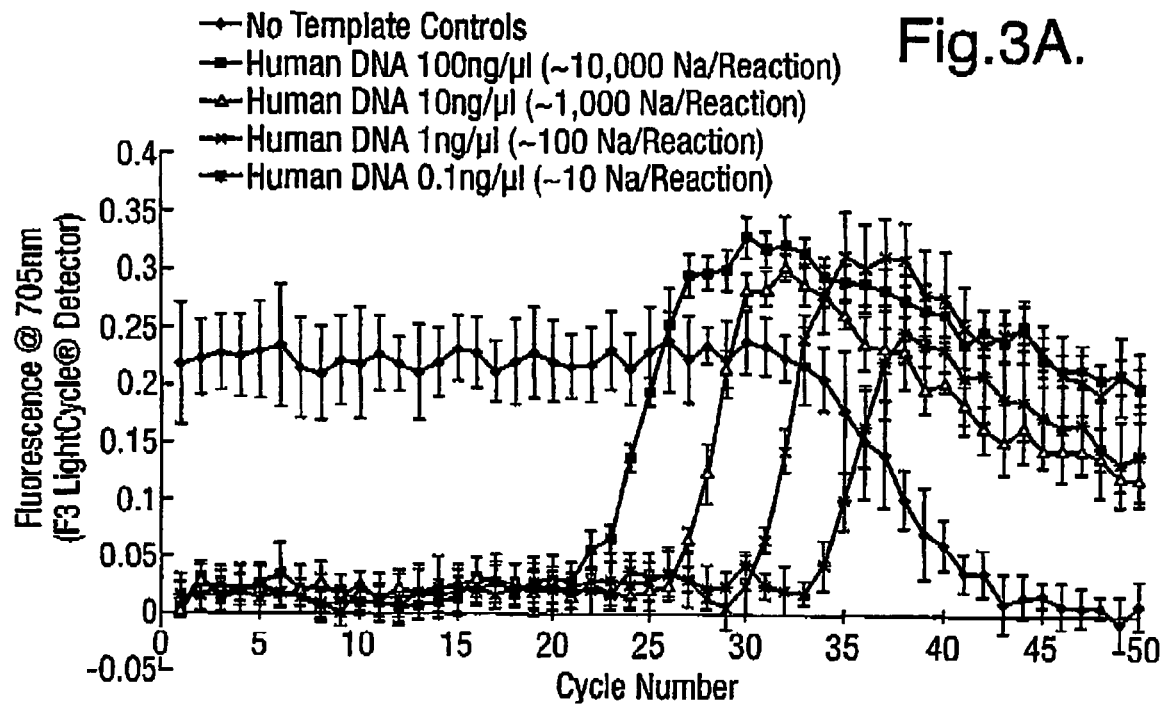
Figure 3B:
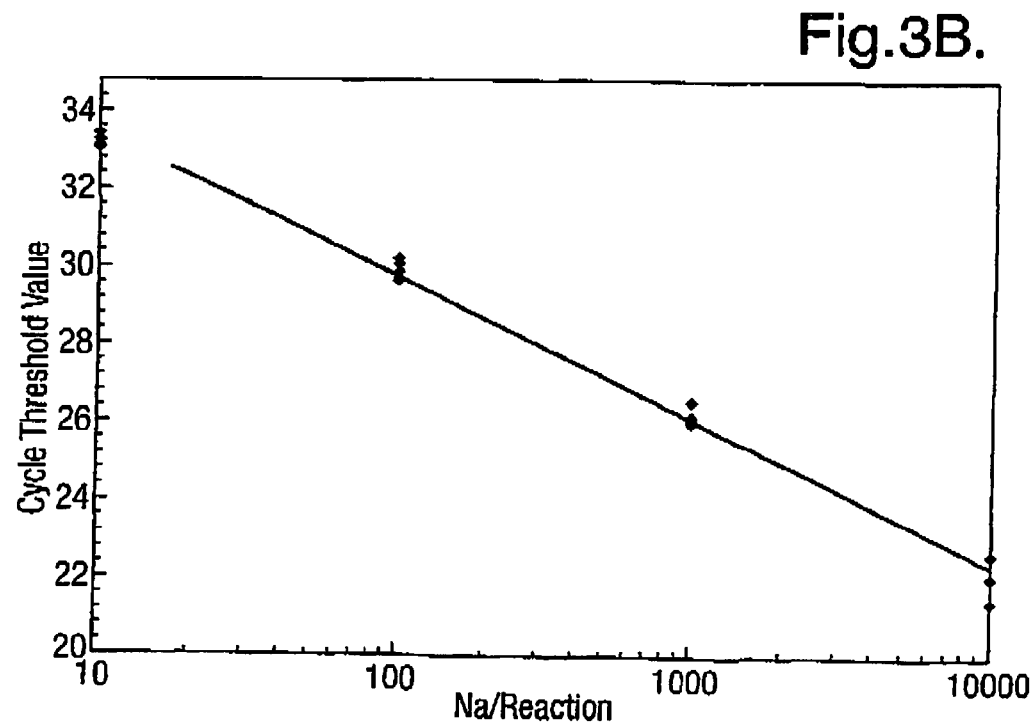

FIG. 3 shows comparative data obtained using assays of WO99/28500 for the beta-actin gene. FIG. 3A shows the measured fluorescence as a function of cycle number for the beta-actin system as a function of concentration of DNA. The data obtained from the prior art system are noisier than those obtained from the method of the present invention. Furthermore, the gradient of response is sharper using the method of the present invention and the cycle threshold value is also slightly lower using the method of the present invention. A comparison of FIGS. 2B and 3B confirms this observation.

FIG. 4 shows comparative data obtained using the Taqman™ assays in accordance with a prior art method. The response curves are relatively shallow compared to those of the present invention. Furthermore, the Taqman™ methodology is very slow compared to that of the present invention.

EXAMPLE 2

Identification and Quantification of porA Gene

FIG. 5 shows fluorescence as measured by the F3 detector as a function of cycle number for the meningitis system for various concentrations of human DNA using the method of the present invention. The data shown use the reagent of structure Seq. No. 5. Each set of data shows a low-level background response for a given number of cycles, dependent on the concentration of DNA within the sample. Within each set of data, the observed fluorescence increases dramatically at a certain cycle number dependent on the concentration of human DNA in the sample.

FIG. 6 shows comparative data obtained using assays of WO99/28500 for the porA gene.

FIG. 7 shows comparative data obtained using the Taqman™ methodology of the prior art. Again, the response curves are relatively shallow compared to those of the present invention. Furthermore, the Taqman™ methodology is very slow compared to that of the present invention. The Taq-Man™ response curves are noisier and the quantification curve generated from such data produces a lower correlation co-efficient than the present method.

EXAMPLE 3

Identification and Quantification of Ct Plasmid Gene

FIG. 8 shows fluorescence as measured by the F3 detector as a function of cycle number for the chlamydia system for various concentrations of human DNA using the method of the present invention. Each set of data shows a low-level background response for a given number of cycles, dependent on the concentration of DNA within the sample. Within each set of data, the observed fluorescence increases dramatically at a certain cycle number dependent on the concentration of human DNA in the sample.

FIG. 9 shows comparative data obtained using the Taqman™ methodology of the prior art. Again, the response curves are relatively shallow compared to those of the present invention. Furthermore, the Taqman™ methodology is very slow compared to that of the present invention.

EXAMPLE 4

Identification and Quantification of CP4 EPSPS Gene

FIG. 10 shows fluorescence as measured by the F3 detector as a function of cycle number for the genetically modified soybean system for various concentrations of the modified gene using the method of the present invention. The figure also shows the fluorescence generated by the lect system as a function of cycle number for various concentrations of the modified gene. Within each set of data the observed fluorescence increases dramatically at a certain cycle number dependent on the concentration of the relevant gene in the sample. The lect system is effectively acting as a control, the fluorescence versus cycle number response curve as expected being virtually independent of the concentration of the modified gene. In the case of the modified gene system, it can be seen that an increase in concentration of the modified gene causes a decrease in the cycle number at which the fluorescence dramatically increases.

FIG. 11 shows comparative data obtained using the Taqman™ methodology of the prior art. Again, the response curves are relatively shallow compared to those of the present invention. Furthermore, the Taqman™ methodology is very slow compared to that of the present invention.

It should be noted that in virtually all circumstances the data obtained using the Taqman™ methodology of the prior art is noisier than those obtained using the method of the present invention. Furthermore, the response curves are shallower than those of the present invention and the quantification curves generated from the data obtained using the method of the present invention have higher correlation co-efficients than those obtained from the Taqman™ methodology.

The present invention also provides a method which is potentially very fast. The data presented herein for the method of the present invention were obtained using the instrumentation at the fastest possible mode of operation. It is believed that the relatively short probe length helps to produce a fast response. It is thus anticipated that the speed of the present method is limited by the current specification of the instrument on which the method is performed.

The invention claimed is:

1. A method for detecting the presence of a target nucleic acid sequence in a sample, the method comprising: performing nucleic acid amplification on the sample in the presence of (a) a DNA duplex binding agent in an unbound state, (b) a nucleic acid polymerase and (c) a reagent comprising an amplification primer which can hybridise to the target sequence when in single stranded form and which is connected at its 5' end to a probe which carries a label by way of a chemical linking group, the labelled probe being of a sequence such that the labelled probe hybridizes to a complementary region in an amplification product, and wherein the label is able to absorb fluorescence from or donate fluorescent energy to the DNA duplex binding agent; and monitoring fluorescence of the sample.

2. The method of claim 1, said method comprising: (a) adding to a sample suspected of containing the target nucleic acid sequence, the DNA duplex binding agent in an unbound state, the nucleic acid polymerase and the reagent; (b) subjecting said sample to conditions under which the primer hybridises to the target nucleic acid sequence and an amplification product comprising the probe is formed; (c) subjecting said sample to conditions under which the labelled probe hybridises to a complementary region in the amplification product; and (d) monitoring fluorescence of said sample during at least one of steps (b) and (c).

3. The method of claim 1 wherein the amplification product comprises the probe.

4. The method of claim 1 wherein the DNA duplex binding agent is an intercalating dye.

5. The method of claim 1 wherein the DNA duplex binding agent comprises a donor label and the probe comprises the acceptor label.

6. The method of claim 1 wherein the DNA duplex binding agent comprises an acceptor label and the probe comprises the donor label.

7. The method of claim 1 wherein the acceptor label is a fluorescent molecule which emits energy at a characteristic wavelength.

8. The method of claim 7 wherein the acceptor label is a rhodamine dye or Cy5.

9. The method of claim 1 wherein the acceptor label is a dark acceptor.

10. The method of claim 9 wherein the dark acceptor is DABCYL, Methyl Red, a QSY-7 diarylrhodamine dye or 6-(dimethylamino)-2-[4-[4-(dimethylamino)p-henyl]-1,3-butadienyl]-1-ethyl quinolinium perchlorate.

11. The method of claim 1 wherein the amplification reaction comprises a polymerase chain reaction.

12. The method of claim 1 wherein the acceptor molecule is a fluorescent molecule and wherein fluorescence of both the donor and the acceptor molecules are monitored and the relationship between the emissions calculated.

13. The method of claim 1 wherein the fluorescent signal from the sample is monitored throughout the amplification reaction and the results used to quantitate the amount of target sequence present in the sample.

14. The method of claim 1 wherein the amplification reaction is performed in the presence of an additional corresponding amplification primer which is not attached to a labelled probe.

15. A method for detecting nucleic acid amplification comprising: performing nucleic acid amplification on a target polynucleotide in the presence of (a) a nucleic acid polymerase, (b) a DNA duplex binding agent in an unbound state and (c) a reagent comprising an amplification primer which can hybridise to the target sequence when in single stranded form and which is connected at its 5' end to a probe which carries a second label, by way of a chemical linking group, the labelled probe being a sequence that can hybridise to a complementary region in an amplification product, and wherein one of the DNA duplex binding agent or second label comprises a donor label which is able to donate fluorescent energy to the other of the DNA duplex binding agent or second label which comprises an acceptor label able to absorb fluorescent energy from the donor molecule, the primer being capable of hybridizing to the target polynucleotide; and monitoring changes in fluorescence during the amplification reaction.

16. The method of claim 15 wherein the amplification is carried out using a pair of primers which are designed such that only the target nucleotide sequence within a DNA strand is amplified.

17. The method of claim 1 wherein the probe is specific either for a splice region of RNA or an intron in DNA, so that only one of amplified RNA or amplified DNA is detected and/or quantitated.

* * * * *

SEQUENCE LISTING

<160> NUMBER OF SEQ ID NOS: 6

<210> SEQ ID NO 1
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(27)
<223> OTHER INFORMATION: hexaethylene glycol (HEG) linker from
      nucleotide at position 26 to nucleotide at position 27

<400> SEQUENCE: 1
atgccctccc ccatgccatc ctgcgtcagc ggaaccgctc attgccaatg g            51

<210> SEQ ID NO 2
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(27)
<223> OTHER INFORMATION: hexaethylene glycol (HEG) linker from
      nucleotide at position 26 to nucleotide at position 27

<400> SEQUENCE: 2
tgccttcttt ctcgcaccaa ttgacacctg catgtgtttg tggctt                  46

<210> SEQ ID NO 3
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(23)
<223> OTHER INFORMATION: hexaethylene glycol (HEG) linker from
      nucleotide at position 22 to nucleotide at position 23

<400> SEQUENCE: 3
ccttcatgtt cggcggtctc gcatgcgcgt ttcaccgct                          39

<210> SEQ ID NO 4
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(22)
<223> OTHER INFORMATION: hexaethylene glycol (HEG) linker from
      nucleotide at position 21 to nucleotide at position 22

<400> SEQUENCE: 4
tcagcggcag cgtccaattc gacttgctgt tttgggccg                          39

<210> SEQ ID NO 5
<211> LENGTH: 38
<212> TYPE: DNA
<213> ORGANISM: Artificial Sequence
<220> FEATURE:
<223> OTHER INFORMATION: Synthetic

```
-continued

<220> FEATURE:
<221> NAME/KEY: misc_feature
<222> LOCATION: (21)..(22)
<223> OTHER INFORMATION: hexaethylene glycol (HEG) linker from
      nucleotide at position 21 to nucleotide at position 22

<400> SEQUENCE: 5
ccaaacgcac ttccgccatc gtcagccaag cgccagac                              38

<210> SEQ ID NO 6
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (35)..(36)
<223> OTHER INFORMATION: hexaethylene glycol (HEG) linker from
      nucleotide at position 35 to nucleotide at position 36

<400> SEQUENCE: 6
tatgcttaca catttatcga ctgggtgatt acagcttttc gtctcttttt cgcagc         56
```